(12) United States Patent
Lee et al.

(10) Patent No.: US 10,473,730 B2
(45) Date of Patent: Nov. 12, 2019

(54) DEFECT DETECTION DEVICE ENABLING EASY REMOVAL OF MAGNETIC IMPURITIES

(71) Applicant: INDUSTRY-ACADEMIC COOPERATION FOUNDATION CHOSUN UNIVERSITY, Gwangju (KR)

(72) Inventors: Jin Yi Lee, Gwangju (KR); Jung Min Kim, Gwangju (KR); Myung Chul Jung, Gwangju (KR); Ji Su Kim, Gwangju (KR)

(73) Assignee: INDUSTRY-ACADEMIC COOPERATION FOUNDATION CHOSUN UNIVERSITY, Gwangju (KR)

(*) Notice: Subject to any disclaimer, the term of this patent is extended or adjusted under 35 U.S.C. 154(b) by 197 days.

(21) Appl. No.: 15/787,001

(22) Filed: Oct. 18, 2017

(65) Prior Publication Data

US 2018/0113177 A1 Apr. 26, 2018

(30) Foreign Application Priority Data

Oct. 20, 2016 (KR) .................. 10-2016-0136268

(51) Int. Cl.
*G01N 27/82* (2006.01)
*G01R 33/00* (2006.01)
*G01N 27/90* (2006.01)

(52) U.S. Cl.
CPC ......... *G01R 33/0017* (2013.01); *G01N 27/90* (2013.01); *G01R 33/0047* (2013.01); *G01R 33/0076* (2013.01); *G01N 27/9006* (2013.01)

(58) Field of Classification Search
CPC ............ G01R 33/0017; G01R 33/0076; G01R 33/0047; G01N 27/82; G01N 27/87; G01N 27/90; G01N 27/9006
See application file for complete search history.

(56) References Cited

U.S. PATENT DOCUMENTS 7,859,256 B1 * 12/2010 Hoyt .................. G01N 27/87
324/220

FOREIGN PATENT DOCUMENTS

| JP | 2001-009322 A | 1/2001 |
| KR | 10-2013-0130529 A | 12/2013 |
| KR | 10-2014-0013237 | 2/2014 |

OTHER PUBLICATIONS

Office action dated Jun. 7, 2017 from Korean Patent Office in a counterpart Korean Patent Application No. 10-2016-0136268.

* cited by examiner

*Primary Examiner* — Minh N Tang
(74) *Attorney, Agent, or Firm* — The PL Law Group, PLLC

(57) ABSTRACT

A defect detection device enables easy removal of magnetic impurities. The defect detection device has a structure capable of effectively removing magnetic impurities adhered to a magnetic flux leakage detection device for nondestructive inspection of a small-diameter heat transfer tube or a partially saturated eddy current detection system. With the defect detection device, it is possible to minimize adhesion of magnetic impurities that deteriorate the performance of a leakage magnetic flux detection device for nondestructive inspection of a small-diameter tube of ferromagnetic metal material or a partially saturated eddy current detection system. Further, there is an advantage in that it is possible to remove the adhered magnetic impurities from the defect detection device easily.

15 Claims, 3 Drawing Sheets

DEFECT DETECTION DEVICE ENABLING EASY REMOVAL OF MAGNETIC IMPURITIES

CROSS REFERENCE TO RELATED APPLICATION

The present application claims priority to Korean Patent Application No. 10-2016-0136268, filed Oct. 20, 2016, the entire contents of which are incorporated herein for all purposes by this reference.

BACKGROUND

1. Field of the Invention

The present invention generally relates to a defect detection device which enables easy removal of magnetic impurities. More particularly, the present invention relates to a defect detection device having a structure capable of effectively removing magnetic impurities adhered to a magnetic flux leakage detection device for nondestructive inspection of a small-diameter heat transfer tube or a partially saturated eddy current detection system.

2. Description of the Related Art

A heat transfer tube is used to transfer heat energy by allowing high and low temperature mediums to flow within a thin metal walled tube. At this time, cracks, corrosion defects, or abrasion may occur in the metal wall of the heat transfer tube due to high temperature, high pressure, impurities, and a flow and a chemical reaction of the medium.

Since such heat transfer tubes are generally small-sized and bundled, it is difficult to inspect such heat transfer tubes from the outside with a defect detection device. Therefore, the heat transfer tube is generally inspected by inserting the defect detection device into the heat transfer tube.

On the other hand, the heat transfer tube can be used until the next inspection period when a certain thickness of the heat transfer tube remains such that corrosion and abrasion of the heat transfer tube are maintained below a certain allowable value. However, in a case of fatigue cracks in the heat transfer tube, maintenance or replacement should be performed.

Therefore, it is necessary to quantitatively evaluate corrosions, abrasions, and fatigue cracks of the heat transfer tube for accurate determination thereof.

As a conventional technique for solving this problem, a nondestructive testing method of the heat transfer tube using a bobbin type coil, annular array magnetic sensors, or cylindrical array magnetic sensors has been developed.

On the other hand, when a material of the heat transfer tube is a ferromagnetic substance, a method of detecting and evaluating the defects by magnetizing a measurement region of the heat transfer tube which is to be measured and measuring a distribution of the leakage magnetic flux generated around the defects is generally used.

As another method, in a case of applying an eddy current detection to inspect the heat transfer tube of the ferromagnetic substance material, the heat transfer tube has a high permeability and thus it is difficult for the eddy current to penetrate into inside of the test piece, whereby the eddy current detection should be performed after partially self-saturating the heat transfer tube.

Alternatively, a remote field eddy current detection is performed such that two or more coils may be coaxially arranged to be separated a distance two or more times larger than a coil diameter.

FIG. 1 is a view showing a nondestructive inspection method using a conventional partially saturated eddy current detection system.

Referring to FIG. 1, an outer diameter of the defect detection device 20 is smaller than an inner diameter of the tube 10 so as to be inserted into the test piece 10 which is a tube of small diameter.

Magnets 40a, 40b, and 40c for magnetizing the test piece 10 by applying a magnetic field thereto are built within the defect detection device 20. An eddy current detecting coil 30 for applying an alternating current to a magnetized area is provided at a central portion of each magnetic pole of the magnets.

When the test piece 10 is magnetized by the magnets 40a, 40b, and 40c, a leakage magnetic flux is generated around the defect. Measuring such leakage magnetic flux using the defect detection device 20 makes it possible to evaluate whether there is a defect and the magnitude thereof. On the other hand, when an AC current is applied to the coil 30 in a partially saturated state, a partially saturated eddy current detection can be applied.

However, according to the conventional technology described above, when the defects of the test piece 10 are inspected, there is a problem in which magnetic impurities adhere to the defect detection device 20. In this case, because the test piece 10 cannot be sufficiently magnetized, there are disadvantages that the defect detection capability and the quantitative evaluation performance are deteriorated.

Further, in a case of the remote field eddy current detection, since an interval between two or more coils must be wide, the length of the sensor itself becomes long and therefore there is disadvantageously a limitation in inspecting a bending tube.

Further, there are disadvantages that a capability of detecting defects in an axial direction is deteriorated in a case of the leakage magnetic flux detection, and a capability of detecting defects in an arc direction is deteriorated in a case of the remote field eddy current detection or the partially saturated eddy current detection.

The foregoing is intended merely to aid in the understanding of the background of the present invention, and is not intended to mean that the present invention falls within the purview of the related art that is already known to those skilled in the art.

SUMMARY

The inventors of the present invention have completed the present invention by developing a structure that can easily remove magnetic impurities adhered to a partially saturated defect detection device having the magnets.

It is therefore an aspect of the present invention to provide a defect detection device which enables minimizing adhesion of the magnetic impurities or enables easy removal of the magnetic impurities even if the impurities are adhered thereto.

It is another aspect of the present invention to provide a defect detection device which enables easy removal of the magnetic impurities even when a measured object is stored without inspecting defects thereof.

A further aspect of the present invention is to provide a defect detection device enabling easy removal of magnetic impurities that may be adhered to a bending tube, because a length of the sensor unit is shorter compared with a remote field eddy current inspection method used for inspection of a heat transfer tube of a ferromagnetic material.

It is still another aspect of the present invention to provide a defect detection device that is capable of simultaneously carrying out the leakage magnetic flux detection method that makes it easy to detect a circular defect and the partially saturated eddy current detection method that makes it easy to detect defects in an axial direction.

The aspects of the present invention are not limited to the above-mentioned aspects, and other aspects not mentioned can be clearly understood by those skilled in the art from the following description.

In order to accomplish the above aspect, the present invention provides a defect detection device enabling easy removal of magnetic impurities, the defect detection device comprising: a main body of cylindrical shape housing a magnet for magnetizing a measured object and having internal threads formed in opposite ends thereof; a sensor unit provided with a plurality of magnetic sensors along an outer surface of the main body; a coil wound around an outer surface of the sensor unit; a protective casing surrounding the main body provided with the sensor unit and the coil; a first support and a second support that are hollow and are coupled to opposite ends of the protective casing respectively; a first fixture and a second fixture respectively passing through the first support and the second support and engaged with the internal threads formed in the opposite ends of the main body; and a magnetic impurity removal cap that is hollow and is coupled to one end of the protective casing in a state in that the first support and the first fixture have been removed.

According to an exemplary embodiment, to remove magnetic impurities, the first support and the first fixture are removed, the magnetic impurity removal cap is coupled to the end of the protective casing, and then the magnet is pulled out of the main body using a ferromagnetic material having a magnetic force larger than that of the magnet, whereby the magnetic impurities adhered to the protective casing are attracted to the magnetic impurity removal cap and removed from the protective casing.

According to an embodiment, the magnetic impurity removal cap may be provided with stepped portions of which outer diameters are increasing from a leading portion that is coupled to the protective casing.

According to an embodiment, the defect detection device further includes a fitting engaged with internal threads formed in one end of the second fixture and connecting a transfer pipe for protecting wiring connected to the coil and the sensor unit with the second fixture.

According to an embodiment, the portion of each of the first support and the second support that is coupled to the protective casing may be formed of a flexible elastic body so as to maintain a gap with an inner wall of the measured object.

According to an embodiment, the first support and the second support may be secured to none of the protective casing, the first fixture, and the second fixture and are therefore rotatable.

According to an embodiment, the main body may have a magnet housing portion for housing the magnet therein and a wiring passage portion.

According to an embodiment, the main body may be formed of a non-metallic material or a non-magnetic material.

According to an embodiment, the magnet may be formed in a cylindrical shape.

According to an embodiment, the protective casing may be made of or coated with a material having a property chemically opposite to that of the magnetic impurities According to an embodiment, the magnetic impurity removal cap may be formed of a non-metallic material or a non-magnetic material.

According to an embodiment, the defect detection device further includes a storage casing having a space to house the defect detection device therein and formed of a non-magnetic material, and the storage casing may be provided with a core of a ferromagnetic material and a coil of a removable element at a portion corresponding to a position of the sensor unit.

According to an embodiment, the portion of the storage casing in which the core and the coil are provided may have a stepped shape with an outer diameter smaller than that of a portion made of the non-magnetic material.

According to an embodiment, an impedance or a phase difference of the coil wound around the outer surface of the sensor unit may be output.

According to an embodiment, an alternating magnetic field distribution locally distorted may be output by the sensor unit provided with the plurality of magnetic sensors.

The present invention has superior advantages as follows.

First, according to a defect detection device enabling easy removal of magnetic impurities of the present invention, it is possible to minimize adhesion of magnetic impurities that deteriorate the performance of a leakage magnetic flux detection device for nondestructive inspection of a small-diameter tube of ferromagnetic metal material or a partially saturated eddy current detection system.

Further, according to a defect detection device enabling easy removal of magnetic impurities of the present invention, there is an advantage in that it is possible to remove the adhered magnetic impurities from the defect detection device easily.

Further, according to a defect detection device enabling easy removal of magnetic impurities of the present invention, there is an advantage in that the magnetic impurities may be easily removed even when a measured object is stored without detecting the defects thereof.

Further, according to a defect detection device enabling easy removal of magnetic impurities of the present invention, there is an advantage in that it is easy to inspect the heat transfer tube that is bended since the device is short compared with a probe for used in a remote field eddy current detection.

Further, according to a defect detection device enabling easy removal of magnetic impurities of the present invention, there is an advantage in that arc defect detection may be easily performed compared with partially saturated eddy current detection.

Further, according to a defect detection device enabling easy removal of magnetic impurities of the present invention, there is an advantage in that axial defect detection may be easily performed compared with magnetic flux leakage detection.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION

Figure 1:
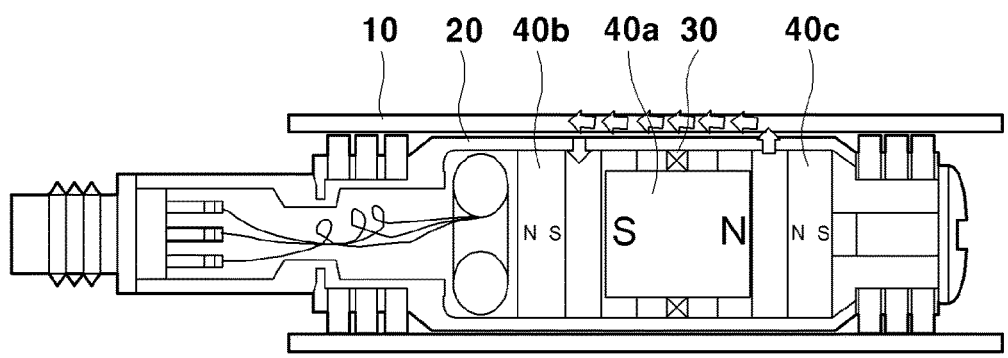
FIG. 1 is a view showing a nondestructive inspection method using a conventional partially saturated eddy current detection system.

The terms used in the present invention are general terms that are widely used at present. However, in some cases, some terms are selected by applicant. In this case, meanings of the terms should be understood considering the terms written in the detailed description part of the invention, not name of simple terms.

Hereinafter, the technical structure of the present invention will be described in detail with reference to exemplary embodiments shown in the accompanying drawings.

However, the present invention is not limited to the embodiments described herein but may be embodied in other forms. Like reference numerals designate like elements throughout the specification.

Figure 2:
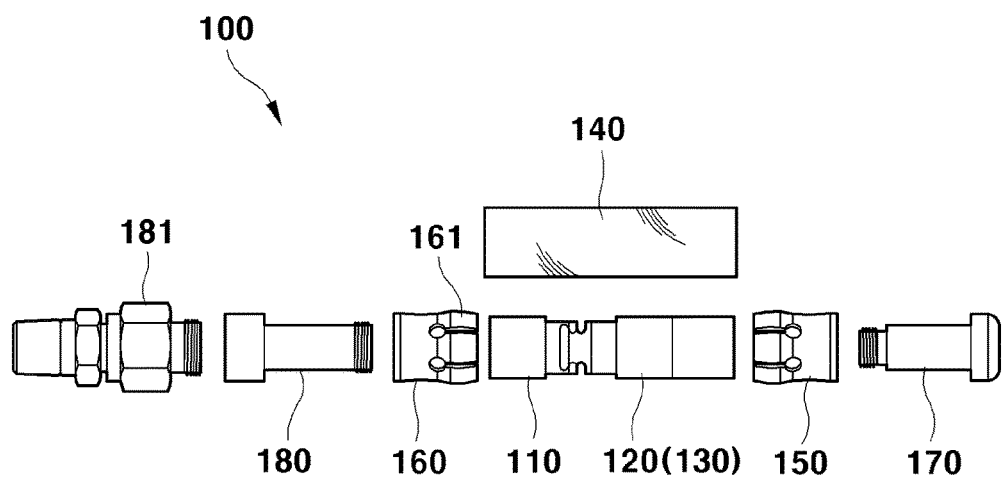
FIG. 2 is an exploded view of a defect detection device which enables easy removal of magnetic impurities according to an embodiment of the present invention.
Figure 3:
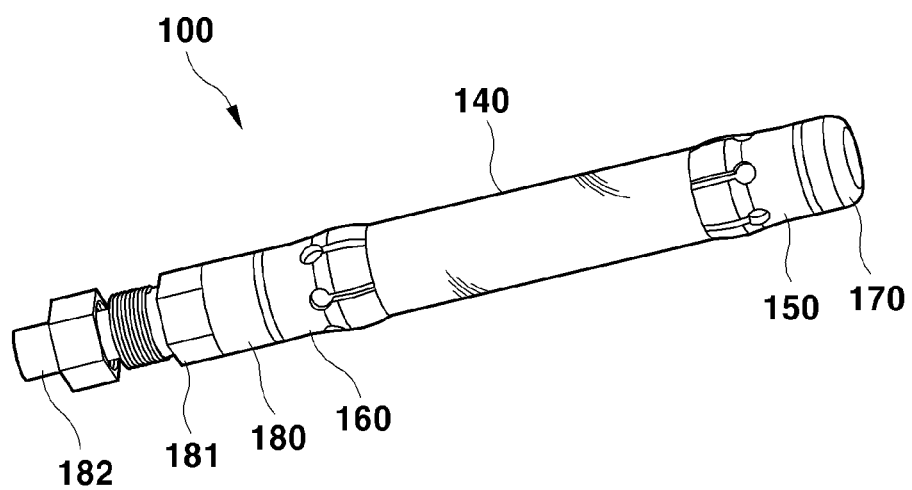
FIG. 3 is an assembled perspective view of a defect detection device which enables easy removal of magnetic impurities according to an embodiment of the present invention.
Figure 4:
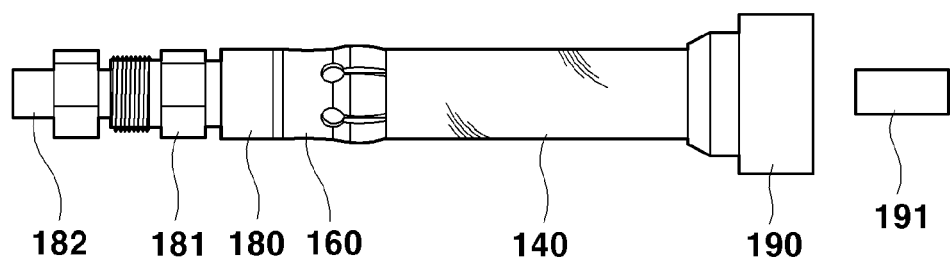
FIG. 4 is a view assembled with a magnetic impurity removal cap of a defect detection device which enables easy removal of magnetic impurities according to an embodiment of the present invention.

FIG. 2 is an exploded view of a defect detection device which enables easy removal of magnetic impurities according to an embodiment of the present invention; FIG. 3 is an assembled perspective view of a defect detection device which enables easy removal of magnetic impurities according to an embodiment of the present invention; and FIG. 4 is a view assembled with a magnetic impurity removal cap of a defect detection device which enables easy removal of magnetic impurities according to an embodiment of the present invention.

Referring to FIG. 2, a defect detection device 100 enabling easy removal of magnetic impurities according to an embodiment of the present invention includes a cylindrical main body 110, a sensor unit 120, a coil 130, a protective casing 140, a first support 150, a second support 160, a first fixture 170, a second fixture 180, and a magnetic impurity removal cap 190.

The main body 110 is configured to secure a magnet for magnetizing a measured object such as a small diameter tube with the sensor unit 120 for detecting a leakage magnetic flux or an eddy current generated in the measured object due to the presence of a defect and a coil 130 for inducing an alternating current in the measured object.

The main body 110 has a magnet housing portion for housing the magnet therein and a wiring passage portion, and is preferably formed in a cylindrical shape to facilitate inserting into a measured object such as a small diameter tube.

The main body 110 has one end on a side of the first support 150 penetrating to enable the magnet to be inserted or removed, and is formed with internal threads to be engaged with the first fixture 170 and the second fixture 180 respectively at opposite ends.

The main body 110 is preferably made of a non-metallic material or a non-magnetic material so as to minimize adhesion of magnetic impurities to the protective casing.

It is preferable that the magnets are provided in a cylindrical shape so as to generate a uniform magnetic field.

It is preferable to use the magnets having a high magnetic force, a residual magnetic flux density high sufficient to facilitate magnetization and demagnetization, and a small coercive force.

When the defect detection device provided with the magnets having the magnetic characteristics described above is used, an object to be measured can be magnetized before carrying out the nondestructive inspection thereof, and then demagnetized after completing the inspection.

The sensor unit 120 is provided around an outer surface of the main body 110, and may include a plurality of magnetic sensors.

The sensor unit 120 may be selected from various types of magnetic sensors, and may be configured such that the plurality of magnetic sensors is arranged in a columnar shape or in a cylindrical shape.

The coil 130 is wound in a way to surround the sensor unit 120 along an outer surface of the sensor unit 120.

The defect detection device 100 enabling easy removal of magnetic impurities according to an embodiment of the present invention includes a power supply unit for applying an current to the coil 130, a data collecting unit for collecting data output from the sensor unit 120, a data processing unit quantitatively quantifying the magnetic flux density distribution of each magnetic sensor according to an intensity of the input current based on the data collected from the data collecting unit, and the like.

The defect detection device 100 enabling easy removal of magnetic impurities according to an embodiment of the present invention is provided with the protective casing 140.

The protective casing 140 surrounds the main body 110, the sensor unit 120, and the coil 130, to protect them in a form of cylindrical tube.

It is preferable that the protective casing 140 is made of or coated with a material having a property chemically opposite to that of magnetic impurities in order to minimize adhesion of magnetic impurities and facilitate removal of the adhered magnetic impurities.

For example, when the magnetic impurities are chemically hydrophilic, a surface of the protective casing 140 may be chemically treated with a hydrophobic material or coated with a hydrophobic material. The surface of the protective casing 140 may be coated with a material such as fluorine that makes it difficult for the impurities to adhere to the surface thereof.

The first support 150 and the second support 160 are coupled to opposite ends of the protective casing 140 respectively, and serve to maintain a gap between the measured object and the magnetic sensor array. Such a gap is called lift-off.

The first support 150 and the second support 160 are provided to be hollow, and the portion coupled to the protective casing 140 is preferably formed with a flexible elastic body so as to maintain a gap with an inner wall of the measured object.

The first support 150 and the second support 160 are secured to none of the protective casing 140, the first fixture 170, and the second fixture 180, and are therefore rotatable.

The first fixture 170 and the second fixture 180 pass through the first support 150 and the second support 160 which are both hollow, and then are engaged with internal threads foamed in opposite ends of the main body 110, respectively.

That is, the first fixture 170 and the second fixture 180 serve to secure the protective casing 140 so as to maintain a predetermined gap therebetween.

The second fixture 180 may be formed to have a through-hole through which a wiring passes.

The second fixture 180 is threaded at opposite ends and engaged with the main body 110 and a fitting 181 which will be described later.

The defect detection device 100 enabling easy removal of magnetic impurities according to an embodiment of the present invention further includes a fitting 181 connecting a transfer pipe 182 to the second fixture 180.

The fitting 181 is connected to the second fixture 180 to allow the transfer pipe 182 to be connected to second fixture for protecting the wiring connecting a power supply and a signal output of the sensor unit 120 and the coil 130 to be connected to the second fixture 180.

The defect detection device 100 enabling easy removal magnetic impurities according to an embodiment of the present invention further includes a magnetic impurity removal cap 190 that is capable of removing magnetic impurities adhered to the protective casing 140.

The magnetic impurity removal cap 190 is provided to be hollow to allow it to be coupled to one end of the protective casing 140, in a state in that the first support 150 and the first fixture 170 have been removed from the protective casing 140.

Preferably, the magnetic impurity removal cap 190 may be provided with stepped portions of which outer diameters are increasing from a leading portion that is coupled to the protective casing 140, and formed of a non-metallic material or a non-magnetic material.

Referring to FIG. 4, it is noted that the first support 150 and the first fixture 170 have been removed and the magnetic impurity removal cap 190 is coupled to one end of the protective casing 140.

The leading portion of the magnetic impurity removal cap 190 coupled to the protective casing 140 is machined to be tapered, and then step-shaped with large steps.

At this time, the magnet is pulled out of the main body using a ferromagnetic body 191 having a magnetic force larger than that of the magnet provided in the magnet receiving portion.

That is, as the magnet is pulled out of the protective casing 140 by the ferromagnetic body 191, the magnetic impurities adhered to the protective casing 140 are magnetically attracted along the tapered portion of the magnetic impurity removal cap 190, and then collected at the stepped portion.

As a result, the magnetic impurities collected in the stepped portion of the magnetic impurity removal cap 190 can be easily removed only by removing the magnetic impurity removal cap 190 from the protective casing 140 and then gently shaking the magnetic impurity removal cap 190.

As described above, according to the defect detection device 100 enabling easy removal of magnetic impurities according to the present invention, there is an advantage in that it is easy to remove magnetic impurities adhered to the protective casing 140.

Meanwhile, according to the defect detection device 100 enabling easy removal of magnetic impurities of the present invention, when the object to be measured is magnetized by the magnet to make permeability constant, and then an alternating current is applied to the coil wound around an outer surface of the sensor unit, an impedance or a phase difference of the coil current due to a presence of the defect can be measured.

According to the defect detection device 100 enabling easy removal of magnetic impurities of the present invention, a leakage magnetic flux caused due to the presence of defects in an arc direction is induced by a magnet for magnetizing a measured object, whereby a flux leakage distribution can be measured by the sensor unit that is provided with a plurality of magnetic sensors.

An alternating magnetic field distribution in which a current of the measured object induced by the coil is locally distorted due to a presence of axial defects is measured by the sensor unit provided with the same plurality of magnetic sensors, whereby the axial defects and arc defects may be easily detected.

Another embodiment of the present invention further includes a storage casing 200 capable of storing the defect detection device 100 according to the embodiment of the present invention.

Figure 5:
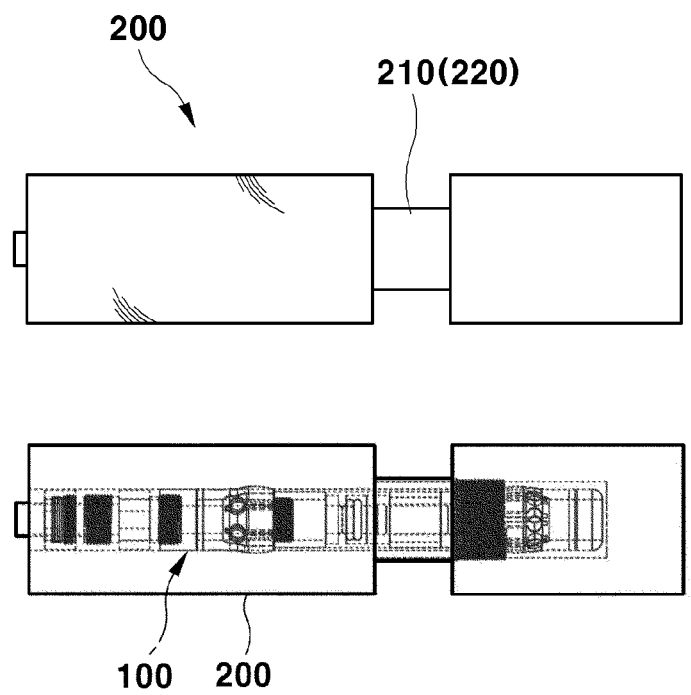
FIG. 5 is a view showing a storage casing of a defect detection device which enables easy removal of magnetic impurities according to an embodiment of the present invention.

FIG. 5 is a view showing a storage casing of a defect detection device enabling easy removal of magnetic impurities according to an embodiment of the present invention.

Referring to FIG. 5, the storage casing 200 has a space for housing the defect detection device 100 therein.

The storage casing 200 is preferably made of a non-metallic material or a non-magnetic material in order to minimize adhesion of magnetic impurities. The storage casing 200 may be cylindrical in order to easily house the defect detection device 100.

It is preferable that the storage casing 200 is formed to have a thickness sufficient to cause the magnetic force to be insignificant in order to minimize adhesion of magnetic impurities during storage of the defect detection device 100.

At this time, the storage casing 200 is provided with a core 210 of a ferromagnetic material and a coil 220 of a removable element at a portion corresponding to a position of the sensor unit 120 of the defect detection device 100.

A portion of the storage casing 200 in which the core 210 and the coil 220 are provided has a stepped shape with an outer diameter smaller than that of a portion made of the non-magnetic material.

That is, in the process of extracting the defect detection device 100 from the storage casing 200, the magnetic impurities adhered to a concave portion (a portion in which the core 210 and the coil 220 are formed) of the storage casing 200 do not come up to the portion of the storage casing 200 made of the non-magnetic material and remains at the concave portion.

As a result, the magnetic impurities collected in the concave portion of the storage casing 200 where the core 210 and the coil 220 are formed may be easily removed only by shaking the storage casing 200 gently, in a state where the detect detection device has been pulled out.

As described above, according to another embodiment of the present invention, even when the defect detection device 100 is being stored, there is an advantage in that the adhered magnetic impurities can be easily removed.

Although exemplary embodiments of the present invention have been described for illustrative purposes, those skilled in the art will appreciate that various modifications, additions and substitutions are possible, without departing from the scope and spirit of the invention as disclosed in the accompanying claims.

The invention claimed is:

1. A defect detection device enabling easy removal of magnetic impurities, the defect detection device comprising:

a main body of cylindrical shape housing a magnet for magnetizing a measured object and having internal threads formed in opposite ends thereof;

a sensor unit provided with a plurality of magnetic sensors along an outer surface of the main body;

a coil wound around an outer surface of the sensor unit;

a protective casing surrounding the main body provided with the sensor unit and the coil;

a first support and a second support that are hollow and are coupled to opposite ends of the protective casing respectively;

a first fixture and a second fixture respectively passing through the first support and the second support and engaged with the internal threads formed in the opposite ends of the main body; and a magnetic impurity removal cap that is hollow and is coupled to one end of the protective casing in a state in that the first support and the first fixture have been removed.

2. The defect detection device of claim 1, wherein, to remove magnetic impurities, the first support and the first fixture are removed, the magnetic impurity removal cap is coupled to the end of the protective casing, and then the magnet is pulled out of the main body using a ferromagnetic material having a magnetic force larger than that of the magnet, whereby the magnetic impurities adhered to the protective casing are attracted to the magnetic impurity removal cap and removed from the protective casing.

3. The defect detection device of claim 2, wherein the magnetic impurity removal cap is provided with stepped portions of which outer diameters increase from a leading portion that is coupled to the protective casing.

4. The defect detection device of claim 3, further comprising:

a fitting engaged with internal threads formed in one end of the second fixture and connecting a transfer pipe for protecting wiring connected to the coil and the sensor unit with the second fixture.

5. The defect detection device of claim 3, wherein the portion of each of the first support and the second support that is coupled to the protective casing is formed of a flexible elastic body so as to maintain a gap with an inner wall of the measured object.

6. The defect detection device of claim 5, wherein the first support and the second support are secured to none of the protective casing, the first fixture, and the second fixture and are therefore rotatable.

7. The defect detection device of claim 3, wherein the main body has a magnet housing portion for housing the magnet therein and a wiring passage portion.

8. The defect detection device of claim 3, wherein the main body is formed of a non-metallic material or a non-magnetic material.

9. The defect detection device of claim 3, wherein the magnet is formed in a cylindrical shape.

10. The defect detection device of claim 3, wherein the protective casing is made of or coated with a material having a property chemically opposite to that of the magnetic impurities.

11. The defect detection device of claim 3, wherein the magnetic impurity removal cap is formed of a non-metallic material or a non-magnetic material.

12. The defect detection device of claim 3, further comprising a storage casing having a space to house the defect detection device therein and formed of a non-magnetic material, wherein the storage casing is provided with a core of a ferromagnetic material and a coil of a removable element at a portion corresponding to a position of the sensor unit.

13. The defect detection device of claim 12, wherein the portion of the storage casing in which the core and the coil are provided has a stepped shape with an outer diameter smaller than that of a portion made of the non-magnetic material.

14. The defect detection device of claim 1, wherein an impedance or a phase difference of the coil wound around the outer surface of the sensor unit are output.

15. The defect detection device of claim 1, wherein an alternating magnetic field distribution locally distorted is output by the sensor unit provided with the plurality of magnetic sensors.

* * * * *